(12) United States Patent
Oh et al.

(10) Patent No.: US 7,951,396 B2
(45) Date of Patent: May 31, 2011

(54) PREPARATION OF NANOLIPOSOME-ENCAPSULATING PROTEINS AND PROTEIN-ENCAPSULATED NANOLIPOSOME

(75) Inventors: Dahl Kyun Oh, Kangwon-do (KR); Kyun Young Lee, Kangwon-do (KR)

(73) Assignee: Regeron, Inc., Chunchon, Kangwon-do (KR)

( * ) Notice: Subject to any disclaimer, the term of this patent is extended or adjusted under 35 U.S.C. 154(b) by 560 days.

(21) Appl. No.: 11/908,960

(22) PCT Filed: Mar. 28, 2006

(86) PCT No.: PCT/KR2006/001132
§ 371 (c)(1), (2), (4) Date: Sep. 17, 2007

(87) PCT Pub. No.: WO2006/109936
PCT Pub. Date: Oct. 19, 2006

(65) Prior Publication Data
US 2008/0213346 A1    Sep. 4, 2008

(30) Foreign Application Priority Data
Mar. 28, 2005  (KR) .................. 10-2005-0025525

(51) Int. Cl.
*A61K 9/127* (2006.01)
*A61K 38/43* (2006.01)
*A61K 31/00* (2006.01)
*A01N 61/00* (2006.01)

(52) U.S. Cl. .............. 424/450; 424/94.1; 514/1

(58) Field of Classification Search .............. None
See application file for complete search history.

(56) References Cited

U.S. PATENT DOCUMENTS

| | | |
|---|---|---|
| 5,133,908 A | 7/1992 | Stainmesse et al. |
| 6,713,533 B1 | 3/2004 | Panzner |
| 2002/0001613 A1* | 1/2002 | Niemiec et al. ............. 424/450 |
| 2002/0119188 A1* | 8/2002 | Niemiec et al. ............. 424/450 |
| 2004/0180094 A1 | 9/2004 | Joyce |

* cited by examiner

*Primary Examiner* — Robert M Kelly
(74) *Attorney, Agent, or Firm* — The Nath Law Group; Joshua B. Goldberg; Mihsuhn Koh

(57) ABSTRACT

Preparing a nanoliposome for encapsulating a protein includes preparing a dispersion by dispersing a phospholipid in an aqueous solution containing the protein, applying a shearing force to the dispersion; adding an additional amount of the phospholipid to the result of the step of applying the shearing force to the dispersion and then applying a shearing force higher than that of the step of applying the shearing force to the dispersion, and repeating the step of adding the additional amount of the phospholipid and applying the higher shearing force with an additional amount of the phospholipid and a shearing force higher than the prior step to obtain a nanoliposome having a desired diameter and encapsulation efficiency.

15 Claims, 12 Drawing Sheets
(4 of 12 Drawing Sheet(s) Filed in Color)

0.001 U Nanolipo-hGH treated SD rat skin (x40)

Buffer treated SD rat skin 0.001 U hGH treated SD rat skin 0.001 U Nanolipo-hGH treated SD rat skin (x40)

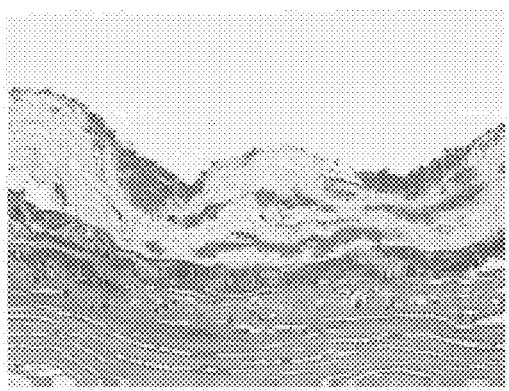 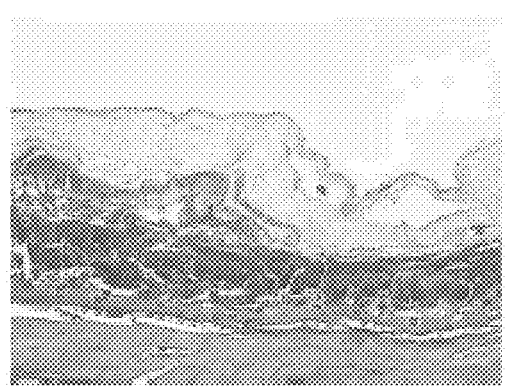
Liposome treated human artificial skin | 0.001U Nanolipo-hGH treated human artificial skin (x100)
FIG. 14 hGH Localization in the Hair Follicle Delivered via Nanolipo-hGH

Non treated mouse skin (X400)

Nanolipo-hGH treated mouse skin (X400)

PREPARATION OF NANOLIPOSOME-ENCAPSULATING PROTEINS AND PROTEIN-ENCAPSULATED NANOLIPOSOME

CROSS-REFERENCES TO RELATED APPLICATIONS

This is a US National Stage of International Application PCT/KR2006/001132, filed with the Republic of Korea Receiving Office on Mar. 28, 2006. The benefit of priority is further claimed to Republic of Korea patent application 10-2005-0025525 filed Mar. 28, 2005.

FIELD OF THE INVENTION

The present invention relates to a method for preparing a nanoliposome-encapsulated proteins and a protein-encapsulating nanoliposome.

DESCRIPTION OF THE RELATED ART

It is generally known in the art that macromolecules such as human growth hormone (molecular weight of about 22 kD) cannot pass through the skin stratum corneum. A molecular weight that can be delivered efficiently through the skin is generally recognized to be no more than about 500 dalton or at most 2 kD even with the help of skin penetration enhancers.

Analysis of skin penetration efficiency is generally performed for medicines. In vivo analysis thereof is carried out by measuring the content of drugs in the blood over time after applying drugs to skin. The in vitro analysis thereof is executed by measuring the skin penetration amount of drugs over time using Frantz cells or artificial skin. Unlike medicines, for cosmetics, it is not always preferable for active ingredients (particularly, human growth hormone) to penetrate into skin to reach blood vessels. For instance, where human growth hormone is used in cosmetics, the following strategies are more desirable: the delivery of human growth hormone to hair follicles of skin to stimulate the receptors for human growth hormone present in skin epidermal stem cells or the cells on the outer root sheath of hair follicles surrounding stem cells, thereby directly or indirectly regulating the rate of skin regeneration; delivery to hair follicle matrix to promote or inhibit hair sprouting or growth, or to regulate melanin biosynthesis; delivery to sebaceous glands to regulate the secretion of sebum; delivery to sweat glands to regulate the secretion of sweat; indirect action on fibroblasts of connective tissues surrounding hair root sheaths to regulate the secretion of elastic fibers; and indirect action on subcutaneous adipocytes to regulate the decomposition of subcutaneous fat.

Nanoliposomes have been suggested to serve as a delivery system for macromolecules such as proteins to the dermis. However, if the transdermal delivery of proteins should be attempted, it is unlikely that nanoliposomes encapsulating proteins such as human growth hormone would penetrate directly into stratum corneum of skin epidermis, considering the compactness of the stratum corneum and the higher molecular weight and hydrophilicity of proteins such as human growth hormone. Instead, it is more reasonable to view any effect of human growth hormone on the dermis is an indirect effect resulting from the delivery of human growth hormone into hair follicles first with the aid of liposomes, then to act on the tissue cells constituting the hair root sheath that lacks developed stratum corneum and thus has a thinner layer to the dermis.

In attempting to employ liposomes as a delivery system for proteins or a means for encapsulating proteins, the following five factors should be considered: (a) encapsulation efficiency of liposomes for proteins; (b) the size distribution of liposomes encapsulating proteins; (c) the applicability of processes for preparing protein-encapsulating liposomes to the industrial scale; (d) the stability of liposomes and proteins during preparation and storage of the liposome-encapsulated proteins; and (e) side effects (that can be) provoked by liposomes.

First, there are considerable factors in seeking processes to elevate the encapsulation efficiency of liposomes. Where drugs are hydrophobic, they are placed in the hydrophobic inner lipid portion (tail portion) of the inner or outer layer of phospholipid bilayer forming liposomes, between the inner and outer layers, or in the inner lipid portions traversing the inner and outer layers. In this case, the encapsulation efficiency is proportional to the total amount of phospholipids constituting liposomes irrespective of the size of liposomes as long as there is little or no repulsion between drugs. However, the total amount of lipids forming unilamellar liposome vesicles dispersed in unit volume of aqueous solution increases as the size of the liposomes decreases. Therefore, the encapsulation efficiency of unilamellar liposomes for hydrophobic drugs increases as the size of liposomes decreases and the amount of liposome-forming lipids increases. In the case of liposomes containing lots of multilamellar vesicles, the content of solution encapsulated in the liposomes decreases per unit lipid amount and the total amount of liposome-forming lipids increases per unit volume of solution, thereby maximizing the encapsulation efficiency for hydrophobic drugs. In contrast, hydrophilic drugs are placed in aqueous solution encapsulated by the lipid bilayer of liposomes. Therefore, the amount of drugs encapsulated in liposomes is proportional to the content of aqueous solution encapsulated in liposomes. When one considers the efficiency of encapsulating hydrophilic drugs with homogeneous concentration into unilamellar liposomes, it is easier to consider the situation into two separate cases; one, in which the amount of lipids forming liposomes is limiting, or the other in which the amount of drugs to be encapsulated in unit liposome is limiting due to the constant size of liposomes. Where the amount of lipids is limiting, the amount of drugs to be encapsulated increases as the size of liposomes increases. Where the amount of drugs to be encapsulated in unit liposome is limiting, i.e., the size distribution of unit liposome is constant, the amount of drugs to be encapsulated increases as the number of unit liposome increases. In most cases, since the size distribution of unilamellar liposomes is constant, the encapsulation efficiency of liposomes for hydrophilic drugs increases as one increases the number of liposomes. Generally, if the size of liposomes is constant, unilamellar liposomes can contain more aqueous solution than multilamellar liposomes.

Secondly, small unilamellar vesicles (SUV) having homogeneous size of no more than 200 nm are preferable for liposomes encapsulating hydrophilic drugs. The smaller size contributes to higher delivery efficiency to target tissues, the homogeneous size distribution to more consistent pharmacokinetic efficacies of the drugs, and the unilamellar structure to higher encapsulation efficiency. The composition and properties of liposomes are optimally determined depending on the delivery mode of drugs to target tissues. For example, where the lipid components comprise cholesterol, the circulating time of liposomes becomes longer in the blood. With respect to liposomes for injections, liposomes circulating in the blood are cleared by reticuloendothelial system and, in general, liposomes are cleared in more rapid fashion as their size and charge are increased. In this regard, small unilamellar vesicles having homogeneous size of no more than 200 nm are preferred for injections.

Third, the process of using a rotating evaporator to make a (dried) phospholipids film and subsequently liposomes, usually performed in the laboratory, by mixing through agitation with an aqueous solution of drugs to be incorporated into liposomes, has some advantages such as higher encapsulation efficiency. However, this process is not suitable for mass production. Furthermore, it produces mostly large multilamellar vesicles (LMV). Therefore, in order to convert LMV to unilamellar vesicles, LMVs need to be subjected to several cycles of freezing and thawing, sonication or extrusion to form microparticles of desired sizes. In this regard, a high-pressure homogenizer is very useful in the mass production of small unilamellar vesicles. One of the shortcomings of a homogenizer is a low encapsulation efficiency. Recently, a mass production process for small unilamellar vesicles has been developed to increase encapsulation efficiency. However, this process of increasing encapsulation efficiency results in production of liposomes only in the form of a gel and therefore frequently leads to problems of homogenizer occlusions, which can hinder its commercial applications.

Fourth, the stability of liposomes and drugs during encapsulation and storage can be analyzed by isolating liposomes with GFC (gel filtration chromatography), disrupting liposomes, and finally measuring the amount or activity of the (liposome-encapsulated) drugs. Proteins such as human growth hormone are generally susceptible to losing their activities due to oxidation or conformational changes, upon exposure to the air or passing through homogenizers under high pressure, respectively.

Fifth, the adverse effects of liposomes should be considered. Phospholipids originated from egg and soybean, which are main components of liposomes, have been conventionally used as cosmetic ingredients and known to exert no adverse effects to the skin. Therefore, if protein-encapsulated liposomes with properties of interest can be produced using such phospholipids, those protein-encapsulating liposome formulations will cause no problems to the skin when used as a cosmetic ingredient or a medicine, as they present little possibility of side effects on the skin. Proteins such as human growth hormone are usually produced from microbes such as E. coli or yeast using genetic engineering technologies. In the case using E. coli, endotoxins such as LPS (lipopolysaccharide), which is a main component of the cell wall, should be removed from the proteins and generally can be removed during the purification processes of the proteins.

As for proteins, according to the common knowledge, it appears nearly impossible for proteins of high molecular weights such as human growth hormone per se or liposomes encapsulating them penetrate into the skin stratum corneum to reach epidermal cells, epidermal stem cells or dermal cells. The present invention provides, for the first time, efficacies of (topical) human growth hormone on the skin previously unexpected and a corresponding novel mechanism according to which human growth hormone is delivered to hair follicles with the aid of liposomes to directly act on cells of the (epidermal) tissues constituting hair follicles via interaction with human growth hormone receptors or to indirectly influence cells of the (dermal) tissues surrounding the hair follicles.

Throughout this application, several patents and publications are referenced and citations are provided in parentheses. The disclosure of these patents and publications is incorporated into this application in order to more fully describe this invention and the state of the art to which this invention pertains.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14 is a photograph showing the effect of the present hGH-encapsulating nanoliposome on artificial human skin.

DETAILED DESCRIPTION OF THIS INVENTION

Figure 1:
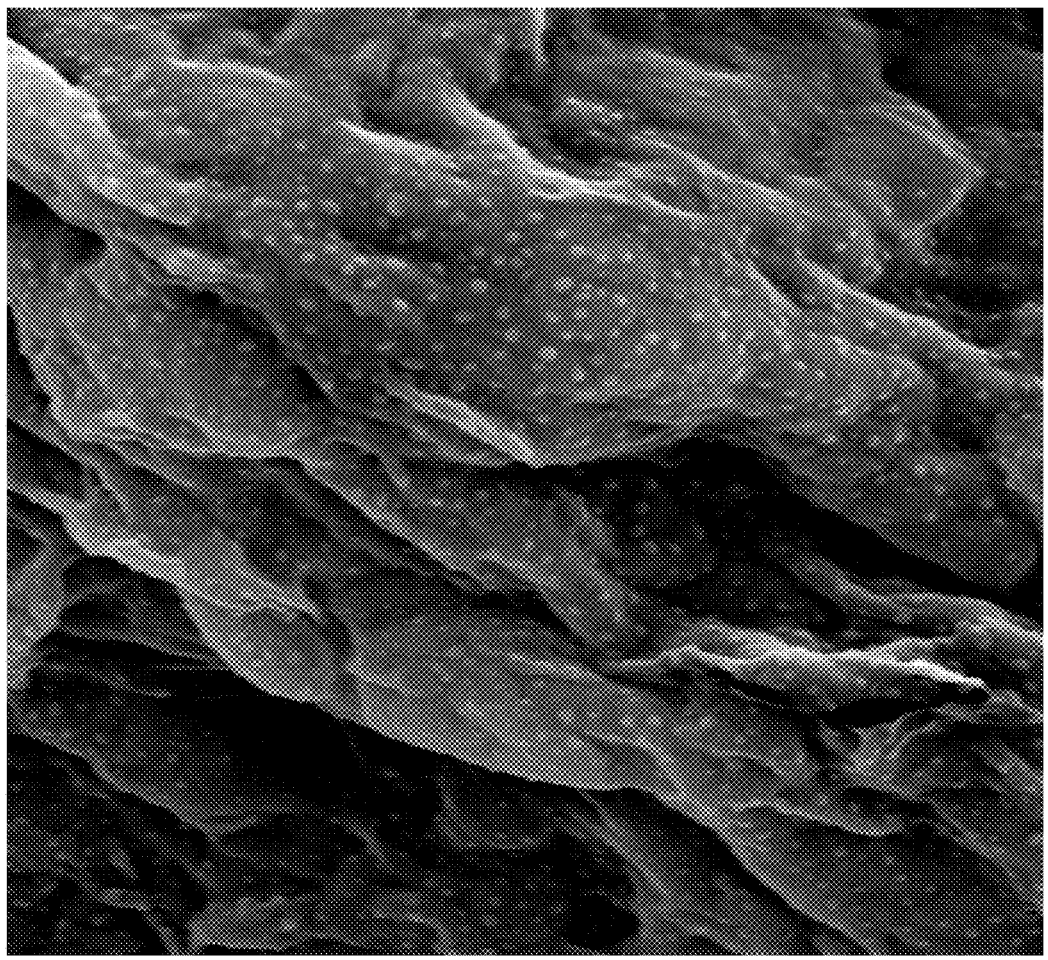
FIG. 1 is an electron microscope photograph of a human growth hormone (hGH)-encapsulating liposome cream formulation (formulation A) prepared according to this invention.

The present inventors have performed intensive research to develop a novel process for preparing nanoliposomes with high encapsulation efficiency for proteins, in the form of a liquid, having a particle size of interest and maintaining its original activity. As results, we have found that a stepwise increase in the shearing forces along with a stepwise addition of phospholipids applied to a composition capable of forming nanoliposomes results in production of protein-encapsulating nanoliposomes having properties of interest described above, thereby enabling us to complete the invention.

Accordingly, it is an object of the present invention to provide a method for preparing a nanoliposome-encapsulated proteins. It is another object of this invention to provide a protein-encapsulating nanoliposome. Other objects and advantages of the present invention will become apparent from the detailed description to follow and in view of the appended claims and drawings.

In one aspect of this invention, there is provided a method for preparing a nanoliposome encapsulating a protein, which includes: (a) preparing a dispersion by dispersing a certain amount of phospholipids in an aqueous solution containing the protein, (b) applying a shearing force to the dispersion, (c) adding an additional amount of phospholipids to the resultant of the step (b) and then applying a shearing force higher than that of the step (b), and (d) repeating step (c) with an additional amount of phospholipids and a shearing force higher than the prior step to obtain nanoliposomes having the intended diameter and encapsulation efficiency.

The present inventors have performed intensive research to develop a novel process for preparing nanoliposomes with high encapsulation efficiency for proteins of high molecular weights, which is in the form of a liquid, having a particle size of interest and maintaining the original protein activity. As results, we have found that a stepwise increase in the shearing forces along with a stepwise addition of phospholipids applied to a composition capable of forming nanoliposomes results in production of protein-encapsulating nanoliposomes having properties of interest described above.

The proteins to be encapsulated in nanoliposomes of this invention are not restricted; they include, but are not limited to, hormones, hormone analogues, enzymes, enzyme inhibitors, signal transduction proteins or fragments thereof, antibodies or fragments thereof, single chain antibodies, binding proteins or fragments thereof, peptides, antigens, adhesive proteins, structural proteins, regulatory proteins, toxin proteins, cytokines, transcription regulatory proteins, blood clotting proteins and plant defense-inducing proteins. Preferably, the protein useful in this invention is a protein hormone, most preferably, human growth hormone (hGH).

In the present invention, proteins dissolved in aqueous solution are used. Preferably, proteins are dissolved in buffers having a buffering power around the optimum pH of the proteins so as to maintain their activities as intact as possible. For instance, it is preferable that proteins having an optimum pH of about 7.0—such as hGH—are dissolved in $NaH_2PO_4$, sodium bicarbonate, imidazole(glyoxaline)-HCl or MOPS having a buffering power around pH 6.5-7.5. Where the present invention is applied to produce hGH-encapsulating nanoliposomes, hGH is preferably dissolved in $NaH_2PO_4$ (pH 6.5-7.5), or more preferably, $NaH_2PO_4$ (pH 6.5-7.5) containing EDTA (ethylene diamine tetraacetic acid). The concentration of $NaH_2PO_4$ in aqueous hGH solution is preferably in the range of 5-100 mM, or more preferably 10-50 mM, and most preferably about 20 mM.

The aqueous protein solution used in this invention may further contain water-soluble salts such as sodium chloride and EDTA to confer a suitable ionic strength for protein stabilization. In addition, the aqueous protein solution may further contain amino acids; water-soluble peptides such as dipeptides, tripeptides and oligopeptides; water-soluble proteins such as collagen; water-soluble sugars such as monosaccharides, disaccharides, trisaccharides and oligosaccharides; water-soluble polysaccharides such as dextrin; water-soluble complex polysaccharides such as chitosan; water-soluble glycosaminoglycan such as chondroitin sulfate and hyaluronic acid; and water-soluble polymers such as PEG (polyethylene glycol) and polyvinyl alcohol.

The term "human growth hormone (hGH)" used herein refers to any polypeptide exhibiting the activity of human growth hormone, for example, any one of mature hGH, Met-hGH, hGH variants, modified-hGH, hGH fragments and hGH analogues. Preferred is mature hGH or Met-hGH. The mature hGH refers to a human growth hormone having the amino acid sequence of the major human growth hormone present in human blood, the Met-hGH refers to a human growth hormone having methionine linked to the N-terminus of mature hGH, the hGH variants refer to human growth hormones having the amino acid sequences of human growth hormones other than the major human growth hormone present in human blood, the modified hGH refers to a human growth hormone modified by linking an additional group such as pegylation or glycation to at least one amino acid residue of human growth hormone, the hGH fragments indicate human growth hormones obtained by deleting a portion of the amino acid sequences of human growth hormones by genetic engineering methods or biochemical methods, and the hGH analogue refers to a human growth hormone obtained by modifying the amino acid sequence of human growth hormone to another amino acid sequence having properties similar thereto by genetic engineering methods.

The term "phospholipids" used herein means any phospholipid capable of forming liposomes unless otherwise indicated, including lecithin (phosphatidyl choline), phosphatidyl serine, phosphatidylethanolamine, phosphatidylglycerol, phosphatidylinositol and sphingomyelin, but not limited to. Preferably, phospholipids useful in this invention are lecithin, most preferably, hydrogenated lecithin. Lecithin can be made from egg, soybean and other plants, most preferably, soybean. Lecithin useful in this invention, which is synthetic, semi-synthetic or natural, includes, but not limited to, soybean lecithin, distearoylphosphatidylcholine, hydrogenated soybean lecithin, egg lecithin, dioleoylphosphatidylcholine, hydrogenated egg lecithin, dielaidoylphosphatidylcholine, dipalmitoylphosphatidylcholine and dimyristoylphosphatidylcholine. Most preferably, phospholipid used in this invention is hydrogenated soybean lecithin.

The dispersion of phospholipids in aqueous protein solution may be carried out according to any conventional process known to one skilled in the art, for example, agitation. In the step for preparing the dispersion for forming liposomes, the concentrations of proteins are generally 0.1-50 mg/ml, preferably 0.2-30 mg/ml, more preferably 0.3-20 mg/ml, most preferably 0.8-3 mg/ml. The initial concentrations of phospholipids are 1-50 w/v %, preferably 2-40 w/v %, more preferably 3-20 w/v %, most preferably 5-10 w/v %, based on the total weight of the dispersed phospholipids. Thereafter, protein-encapsulating liposomes are prepared by applying a shearing force to the dispersion.

The application of shearing force is well known to one skilled in the art, and is preferably performed using a high pressure homogenizer, a sonicator, a microfluidizer, an extrusion apparatus or a French press, most preferably, a high pressure homogenizer.

The most prominent feature of this invention is that the shearing force is applied to the dispersion in a stepwise increasing manner from a low force to a high force, not a constant manner, along with stepwise addition of the phospholipids.

According to a preferred embodiment, the application of a stepwise increase of shearing forces executed by steps (b)-(d) is performed using the high pressure homogenizer with increasing a pressure from 0 to 1200 bar, more preferably, from 0 to 1000 bar, most preferably, from 0 to 800 bar. The pressure of the high pressure homogenizer is preferably increased by 50-200 bar, more preferably by about 100 bar.

According to a preferred embodiment, the amount of phospholipids increased stepwise by steps (a)-(d) is increased from 0 w/v (%) to 30 w/v (%). Preferably, the amount of phospholipids is stepwise increased by the increment of 1-5 w/v (%).

The steps executed in the high pressure homogenizer are preferably carried out at no more than 50° C., more preferably no more than 40° C., still more preferably no more than 30° C., most preferably 25-30° C.

The processing in the homogenizer under each pressure is preferably executed for several cycles, more preferably, for 2-5 cycles. The number of the total cycle by the homogenizer is 5-40, preferably 10-40, more preferably 20-40, most preferably 20-30.

The present invention will be described in more details by illustrating one specific example of this invention. The dispersion capable of forming liposomes containing an amount of a protein and phospholipid is passed through the high pressure homogenizer under 0 bar. This processing is repeatedly performed for 3 cycles. Then, to the resultant, added 1-5 w/v (%) of phospholipid, and is passed through the high pressure homogenizer under 100 bar for 3 cycles. To the resultant, 1-5 w/v (%) of phospholipid is further added and is passed through the high pressure homogenizer under 200 bar for 3 cycles. Such processing with homogenizer is repeatedly carried out with a stepwise increase of pressure up to 800 bar with simultaneous addition of phospholipid (up to 30 w/v (%)), so that protein-encapsulating nanoliposomes having desired properties are finally obtained.

Where nanoliposomes are prepared through a stepwise addition of phospholipids and a stepwise increase of shearing force, the resulting products take on thermodynamically stable forms in a more rapid fashion, generating effects sequentially of increasing solubility of the phospholipids, elevating liposome-forming efficiency and protein-encapsulating efficiency, and of yielding nanoliposomes having properties of interest described previously.

The final nanoliposomes thus obtained have the diameter of 50-350 nm, preferably 50-300 nm, more preferably 100-250 nm, most preferably 150-200 nm. The small sizes of nanoliposomes of this invention facilitate their easy penetration into target tissues.

Nanoliposomes formed by the present method have preferably the structure of a small unilamellar vesicle. According to a preferred embodiment, the nanoliposomes of this invention are in the form of liquid, which can be verified in Example I. According to a preferred embodiment, the present method shows the encapsulation efficiency of no less than 50%. The term "encapsulation efficiency" used herein refers to a ratio of the content of proteins encapsulated in nanoliposomes to the content of proteins contained in an initial protein solution. More preferably, the present method shows the encapsulation efficiency of no less than 70%, still more preferably no less than 80%, most preferably no less than 90%.

It is generally known that high encapsulation efficiency could be accomplished by increasing the content of phospholipids. However, as the content of phospholipids is increased, they are hardly dispersed at room temperature and their viscosity is also increased to be in a gel form, which occludes passages of liposome-forming dispersions in a homogenizer to sharply drop the processivity and production efficiency of a homogenizer. While heating can promote dispersion of phospholipids, proteins such as human growth hormone are prone to denaturation leading to their loss of biological activities generally at temperatures above 60° C.

In contrast, the present invention ensures production of nanoliposomes containing phospholipids preferably up to 20 w/v (%), more preferably up to 25 w/v (%), most preferably up to 30 w/v (%), giving rise to nanoliposomes with much higher encapsulation efficiency.

Where macromolecular proteins such as human growth hormone are intended to be locally delivered to target tissues via skin but not to be delivered systemically or not to affect other tissues than skin, it is very important to produce suitable protein formulations. Since proteins such as human growth hormone are generally unstable in solution to be liable to be denatured, inactivated and decomposed, they hardly possess good stability and long-term storage in solution that are essentially required for protein formulations (particularly, cosmetics) for topical administration to skin.

The present invention overcomes completely the shortcomings arising out of formulations with proteins by suggesting a unique process for producing protein-encapsulating nanoliposomes. Proteins (particularly, hGH) in nanoliposomes prepared by this invention maintain almost their physicochemical properties and activity prior to encapsulation (see Example VII) and show excellent long-term storage (see Example V).

Proteins encapsulated in the finally formed nanoliposome according to this invention has an activity corresponding to at least 60%, preferably at least 70%, more preferably at least 80%, still more preferably 90-100%, most preferably 100% of the activity of proteins prior to encapsulation. Such maintenance in protein activity would be a surprising result compared to conventional technologies.

In the present invention, liposomes encapsulating high-cost proteins such as human growth hormone can be produced in large quantities with higher encapsulation efficiency using high pressure homogenizers and the like in the industry scale, while maintaining the liquid form to enable a continuous production with high productivity.

In another aspect of this invention, there is provided a protein-encapsulating nanoliposome encapsulating a protein, characterized in that the nanoliposome has the diameter of 50-350 nm, has the structure of a small unilamellar vesicle, and is in the form of liquid; wherein the protein encapsulated in the nanoliposome has an activity corresponding to 90-100% of that of the protein prior to encapsulation.

The protein-encapsulating nanoliposome of this invention will be described with referring to descriptions for the present method described hereinabove. For example, descriptions for proteins and phospholipids as liposome components follow those for the present method. Therefore, the common descriptions between them are omitted in order to avoid undue redundancy leading to the complexity of this specification.

The nanoliposomes of this invention have the diameter of 50-350 nm, preferably 50-300 nm, more preferably 100-250 nm, most preferably 150-200 nm. The small size of nanoliposomes of this invention enhances their delivery into target tissues.

According to a preferred embodiment, the nanoliposomes of this invention encapsulate human growth hormone. The nanoliposomes are preferably prepared by the present method described above. According to a preferred embodiment, when the protein-encapsulating nanoliposome of this invention is stored for 10 months at room temperature, the protein maintains an activity corresponding to 72-80% (most preferably 72-78%) of that of the protein prior to encapsulation. In other words, the present nanoliposomes have excellent stability in storage.

The protein-encapsulating nanoliposome of this invention maintains significantly high activity, has a suitable size, most preferably, of 150-200 nm, and has a SUV structure, such that its delivery efficiency to hair follicle as well as penetration efficiency into skin is remarkable to exert various physiological activities in skin. In particular, hGH-encapsulating nanoliposomes of this invention can be applied for improving a variety of skin conditions. Preferably, hGH-encapsulating nanoliposomes of this invention are effective in treatment of acne, improvement of wrinkle, removal of dark spots, improvement of skin elasticity, promotion of hair growth, prevention of skin aging, improvement of skin moisture, and proliferation of dermal stem cells and epidermal stem cells, more preferably, treatment of acne, improvement of wrinkle and promotion of hair growth.

The following specific examples are intended to be illustrative of the invention and should not be construed as limiting the scope of the invention as defined by appended claims.

EXAMPLES

Example I

Preparation of Human Growth Hormone-Containing Liposomes (Nanolipo-hGH)

Formulation A (Cream Formulation): Human Growth Hormone-Containing Cream Formulation Phospholipid used in formulation A was lipoid S100 (Lipoid GmbH, Germany) or lipoid S75 (Lipoid GmbH, Germany). The heat exchanger of a high-pressure homogenizer (max. output 5 L/hr, max. pressure 1200 bar, Model HS-1002; Hwasung Machinery Co., Ltd., South Korea) was placed in ice water such that the temperature of the outlet of the homogenizer did not exceed 30° C., and the inside of the homogenizer was washed with distilled water so as to be ready to operate. Then, to 100 ml of a solution of human growth hormone (LG Life Sciences, Ltd) dissolved in a buffer solution (20 mM $NaH_2PO_4$ pH 6.5-7.5, 1 mM EDTA) at a concentration of 1 mg/ml, phospholipid was added at a ratio of 5 w/v % and sufficiently hydrated and stirred. The stirred solution was passed through the homogenizer three times or more at room temperature under 0 bar. To the solution passed through the homogenizer, phospholipid was added to a ratio of 6 w/v % and sufficiently hydrated and stirred. The stirred solution was passed through the homogenizer three times or more under 100 bar. Then, to the solution passed through the homogenizer under 100 bar, phospholipid was added to a ratio of 7 w/v %, sufficiently hydrated and stirred, and passed through the homogenizer three times or more under 200 bar.

After that, to the solution passed through the homogenizer under 200 bar, phospholipid was added to a ratio of 8 w/v %, sufficiently hydrated and stirred, and passed through the homogenizer three times or more under 300 bar. To the solution passed through the homogenizer under 300 bar, phospholipid was added to a ratio of 9 w/v %, sufficiently hydrated and stirred, and passed through the homogenizer three times or more under 400 bar. Then, to the solution passed through the homogenizer under 400 bar, phospholipid was added to a ratio of 10 w/v %, sufficiently hydrated and stirred, and passed through the homogenizer three times or more under 500 bar. Then, to the solution passed through the homogenizer under 500 bar, phospholipid was added to a ratio of 11 w/v %, sufficiently hydrated and stirred, and passed through the homogenizer three times or more under 600 bar. Thereafter, to the solution passed through the homogenizer under 600 bar, phospholipid was added to a ratio of 12 w/v %, sufficiently hydrated and stirred, and passed through the homogenizer three times or more under 800 bar, thus preparing a human growth hormone-containing liposome (Nanolipo-hGH) cream formulation.

FIG. 1 shows an electron microscope photograph of the human growth hormone-containing liposome cream formulation prepared in this Example. The liposome cream formulation prepared in this Example was coated with gold and observed under a scanning electron microscope (HITACHI S 2500). In the photograph, the bent and connected background is presumed as gel, and small spherical particles are determined as nanoscale loposomes (0.02-0.3 μm).

Formulation B (Liposome Formulation): Human Growth Hormone (hGH)-Containing Liposome Formulation Phospholipid used in the preparation of formulation B was soybean lecithin (ShinDongBang Co. Ltd., South Korea), Metarin P (Degussa Texturant Systems Deutschland GmbH & Co. KG), Nutripur S (Degussa Texturant Systems Deutschland GmbH & Co. KG) or Emultop (Degussa Texturant Systems Deutschland GmbH & Co. KG).

The heat exchanger of a high-pressure homogenizer (max. output 5 L/hr, max. pressure 1200 bar, Model HS-1002; Hwasung Machinery Co., Ltd., South Korea) was placed in ice water such that the temperature of the outlet of the homogenizer did not exceed 30° C., and the inside of the homogenizer was then washed with distilled water so as to be ready to operate. Then, to 100 ml of a solution of human growth hormone (LG Life Sciences, Ltd.) dissolved in a buffer solution (20 mM $NaH_2PO_4$ pH 6.5-7.5, 1 mM EDTA) at a concentration of 1 mg/ml, phospholipid was added at a ratio of 10 w/v % and sufficiently hydrated and stirred. The stirred solution was passed through the homogenizer three times or more at room temperature under 0 bar. Then, to the solution passed through the homogenizer, phospholipid was added to a ratio of 14 w/v %, sufficiently hydrated and stirred, and passed through the homogenizer three times or more under 100 bar. After that, to the solution passed through the homogenizer, phospholipid was added to a ratio of 18 w/v %, sufficiently hydrated and stirred, and passed through the homogenizer three times or more under 200 bar. Then, to the solution passed through the homogenizer, phospholipid was added to a ratio of 20 w/v %, sufficiently hydrated and stirred, and passed through the homogenizer three times or more under 300 bar.

Figure 2:
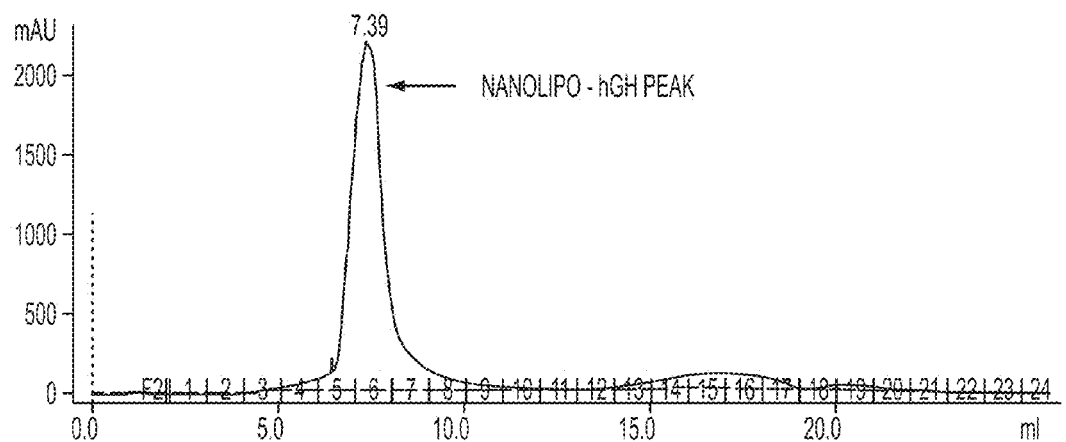
FIG. 2 is a gel permeation chromatogram of an hGH-encapsulating liposome (Nanolipo-hGH) of formulation B prepared according to this invention.

Thereafter, to the solution passed through the homogenizer, phospholipid was added to a ratio of 22 w/v %, and sufficiently hydrated and stirred, and passed through the homogenizer three times or more under 400 bar. To the solution passed through the homogenizer, phospholipid was added to a ratio of 24 w/v %, sufficiently hydrated and stirred, and passed through the homogenizer three times or more under 500 bar. Then, to the solution passed through the homogenizer, phospholipid was added to a ratio of 26 w/v %, sufficiently hydrated and stirred, and passed through the homogenizer three times or more under 600 bar. To the solution passed through the homogenizer, phospholipid was added to a ratio of 28 w/v %, sufficiently hydrated and stirred, and passed through the homogenizer three times or more under 700 bar. Then, the solution passed through the homogenizer under 700 bar was passed through the homogenizer three times or more under 800 bar and discharged from the homogenizer. The discharged solution was subjected to high-speed centrifugation at 15,000×g for 30 min, and the supernatant was separated. At this time, human growth hormone which has not been encapsulated in liposome was removed by gel permeation chromatography (GE Healthcare, USA), thus obtaining liposomes in the form of liquid (see FIG. 2).

Formulation B prepared using a solution of distilled water and buffer solution (20 mM $NaH_2PO_4$, 1 mM EDTA, pH 6.0-7.5) did not show a difference in physical properties and stability of liposomes. Where the finally obtained formulation was stored in more than 10 w/v % of soybean lecithin at 15-30° C. for a long period of time (more than one month), the phase separation (an upper aqueous solution layer, and a lower lipid layer) occurred. However, in less than 10 w/v % of soybean lecithin, the final formulation exhibited excellent stability without phase separation.

Example II

FPLC Separation and SDS-Page Analysis

Figure 3:
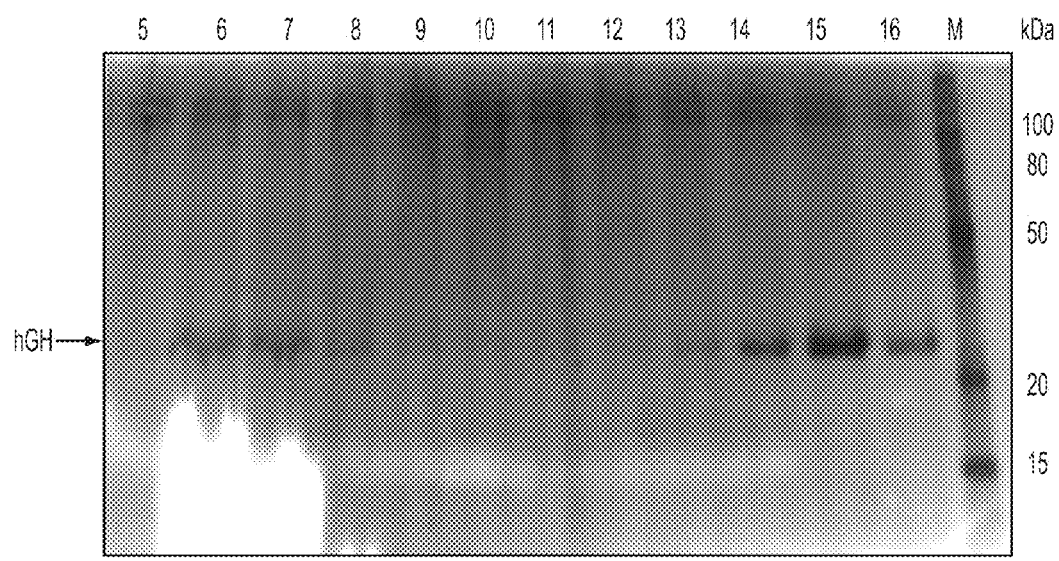
FIG. 3 shows the results of SDS-PAGE for hGH encapsulated in Nanolipo-hGH of formulation B prepared according to this invention.

For the analysis of the human growth hormone-containing liposome of formulation B prepared in Example I, FPLC (Acta explorer, Amersham Bioscience) was equipped with a Superdex 200 HR/30 column at room temperature, and the column was equilibrated with two volumes of a buffer solution (20 mM $NaH_2PO_4$, 1 mM EDTA and 150 mM NaCl). Then, the human growth hormone-containing liposome was separated into fractions which were then collected and analyzed by SDS-PAGE. As shown in FIG. 3, the band of human growth hormone could be observed at about 22 kDa.

Example III

Quantification of Human Growth Hormone in Liposome

Figure 4:
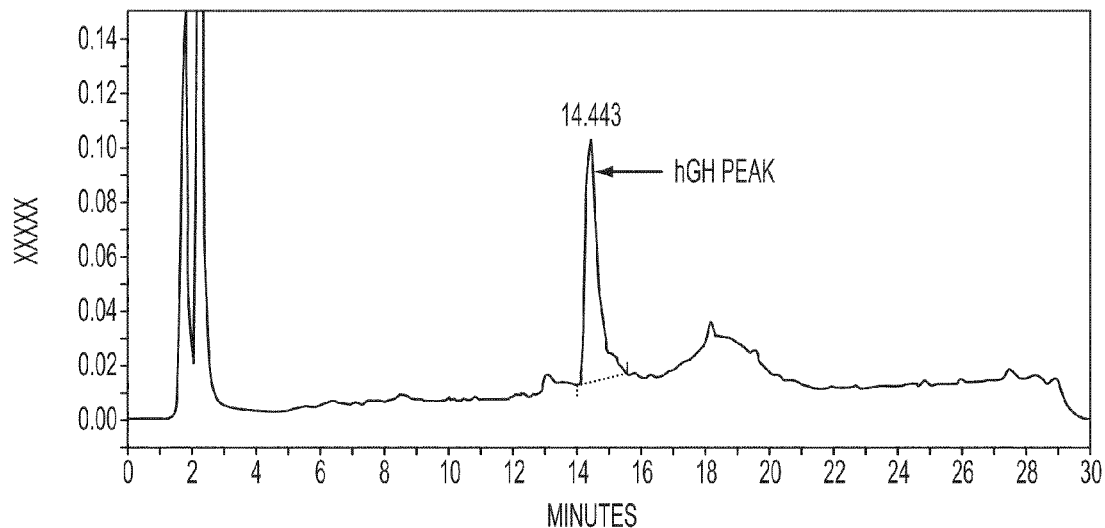
FIG. 4 is a reverse-phase HPLC chromatogram of hGH encapsulated in Nanolipo-hGH of formulation B prepared according to this invention.

HPLC (Shimazu) was equipped with a $C_{18}$ Delta pack column (Waters, USA), and reverse phase-HPLC was performed by a concentration gradient (B 60-10%: 0-25 min, B 60%: 25.01-30 min) at a flow rate of 1 ml/min using 0.1% TFA acetonitrile as solvent A and 0.1% TFA $H_2O$ as solvent B. A standard sample (International Standard human growth hormone NIBSC code 98/574) was quantified using a fluorescence detector (excitation: 295 nm, range: 270-300 nm; emission: 350 nm, range: 300-400 nm) under conditions of oven temperature of 55° C. and run time of 30 min. Then, a sample was pretreated by disrupting the human growth hormone-containing liposome solution with a sonicator and adding a buffer solution (50 mM Tris-Cl pH 8.0, 1 mM EDTA, 8 M urea, 2% Tween 20) thereto in the same volume as the sample and then pipetting the mixture, and was quantified by HPLC using the fluorescence detector (see FIG. 4).

The results reveal that the Nanolipo-hGH of formulation B prepared in Example I contains about 3.69 µg/ml of human growth hormone.

Example IV

Analysis of Phospholipid Content

Figure 5:
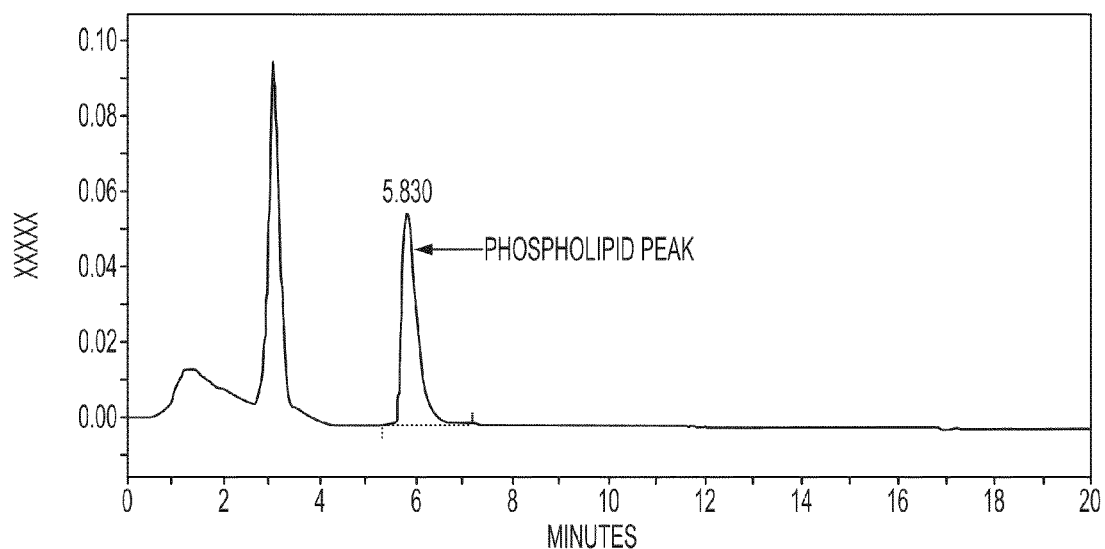
FIG. 5 is a reverse-phase HPLC chromatogram of phospholipids of Nanolipo-hGH of formulation B prepared according to this invention.

HPLC (Shimazu) was equipped with a Spherisorb S5 NH2 column (Waters), and HPLC was performed by isocratic gradient at a flow rate of 1 ml/min using a mixed solvent of 60% acetonitrile, 30% methanol and 5% H2O. Phospholipid was completely dissolved in a mixed solvent of methanol:chloroform (90%:10%) and quantified using a UV light detector (215 nm) under conditions of oven temperature of 35(C and run time of 20 min. The human growth hormone-containing liposome solution of this invention was completely dissolved in a mixed solvent of methanol:chloroform (90%:10%) and then quantified by HPLC according to the same manner as described previously (see FIG. 5).

The quantification results show that the Nanolipo-hGH of formulation B prepared in Example I contains about 3.26 mg/ml of phospholipid.

Example V

Stability Test

Figure 6:
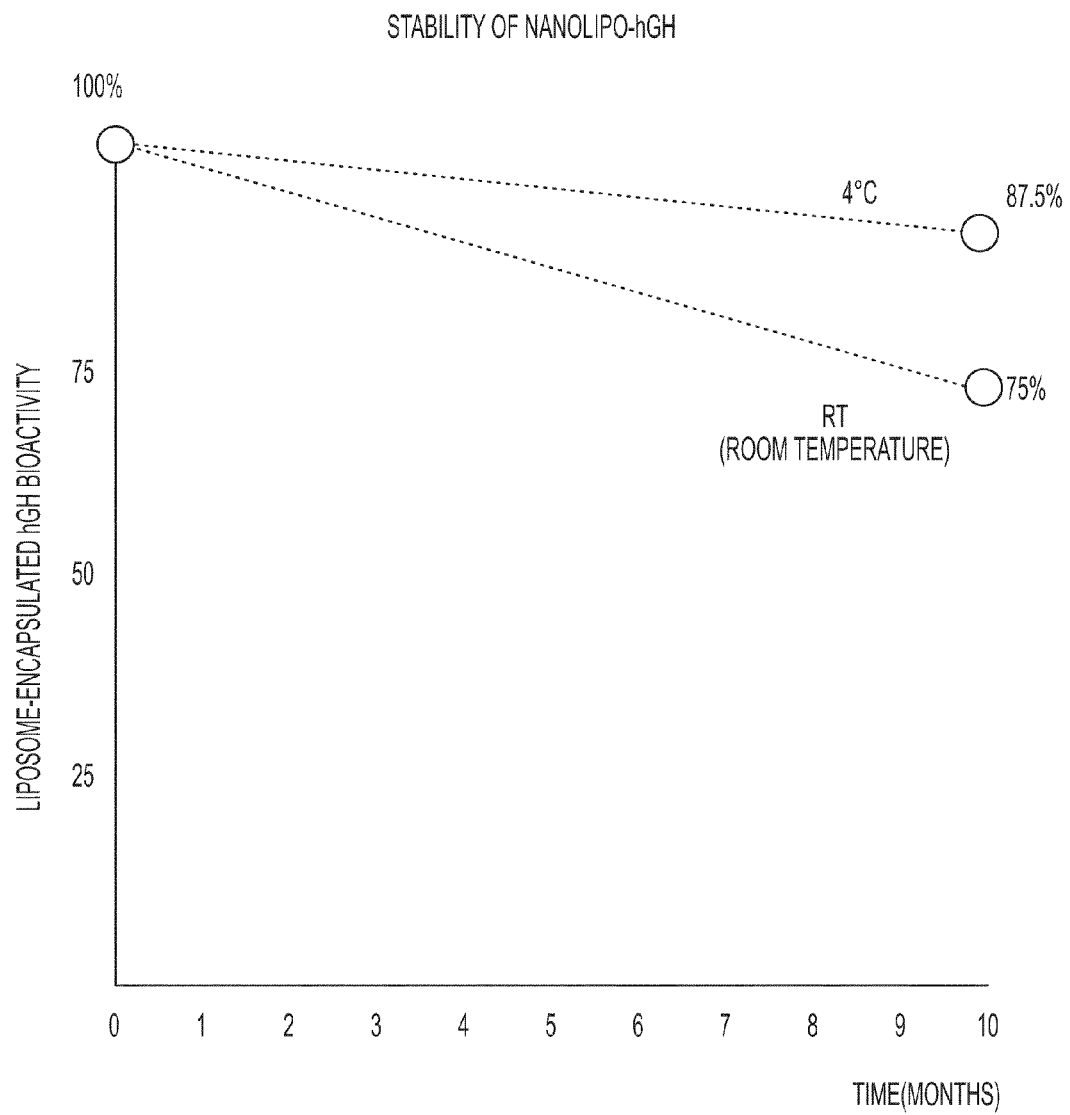
FIG. 6 is a graphic diagram showing the results of the stability test for Nanolipo-hGH of formulation B prepared according to this invention.

A stability test for the human growth hormone-containing liposome of formulation B prepared in Example I was performed in the following manner: The present Nanolipo-hGH containing 0.1% methyl paraben was analyzed for stability by placing it in brown color bottles, standing at 4° C. or 15-30° C. and quantifying the content of hGH by HPLC at one-week intervals. As shown in FIG. 6, the present Nanolipo-hGH after 10 months of storage has initial hGH contents of 87.5% at 4° C. and 75% at room temperature. This result demonstrates that the Nanoipo-hGH of this invention has excellent stability.

Example VI

Safety Test

To test the safety of the present human growth hormone-containing liposome (formulation B prepared in Example I), the cytotoxicities against human keratinocyte cell line HaCaT (DKFZ, Germany) and human embryonic fibroblast HEF (gift from Prof. Lee, Jaeyong, Department of Biochemistry, School of Medicine, Hallym University) were examined.

HaCaT and HEF were suspended in 10% FBS/DMEM (FD media) at concentrations of $1\times10^5$ cells/ml and $5\times10^4$ cells/ml, respectively. 1 ml of each of the suspensions was added to a 24-well plate and then cultured overnight in a 5% $CO_2$ incubator at 37° C. After the culture, the supernatant was carefully removed, and a suitable amount of 10% FD medium and various concentrations of samples were added to the wells of the plate and allowed to incubate overnight in a 5% $CO_2$ incubator at 37° C. The samples used were a buffer solution (containing 20 mM Na—Pi, pH 7.0, 1 mM EDTA and 0.1% methyl paraben), liposome, human growth hormone and the Nanolipo-hGH of formulation B prepared in Example I. After the reaction, the viability of the cells was measured using 3-(4,5-dimethylthiazol-2-yl)-2,5-diphenyltetrazolium bromide (MTT: Sigma, USA) (Shearman et al., *Proc. Natl. Acad. Sci.* 91(4):1470-4 (1994), Shearman et al., *J. Neurochem.* 65(1):218-27 (1995) and Kaneko et al., *J. Neurochem.* 65(6):2585-93 (1995)). The MTT reaction products were measured for absorbance at 570 nm using an ELISA reader (Molecular Devices, USA). The cell viability for each of the samples was expressed as a value relative to the absorbance of a well not containing samples, taken as 100% (FIG. 7).

Figure 7:
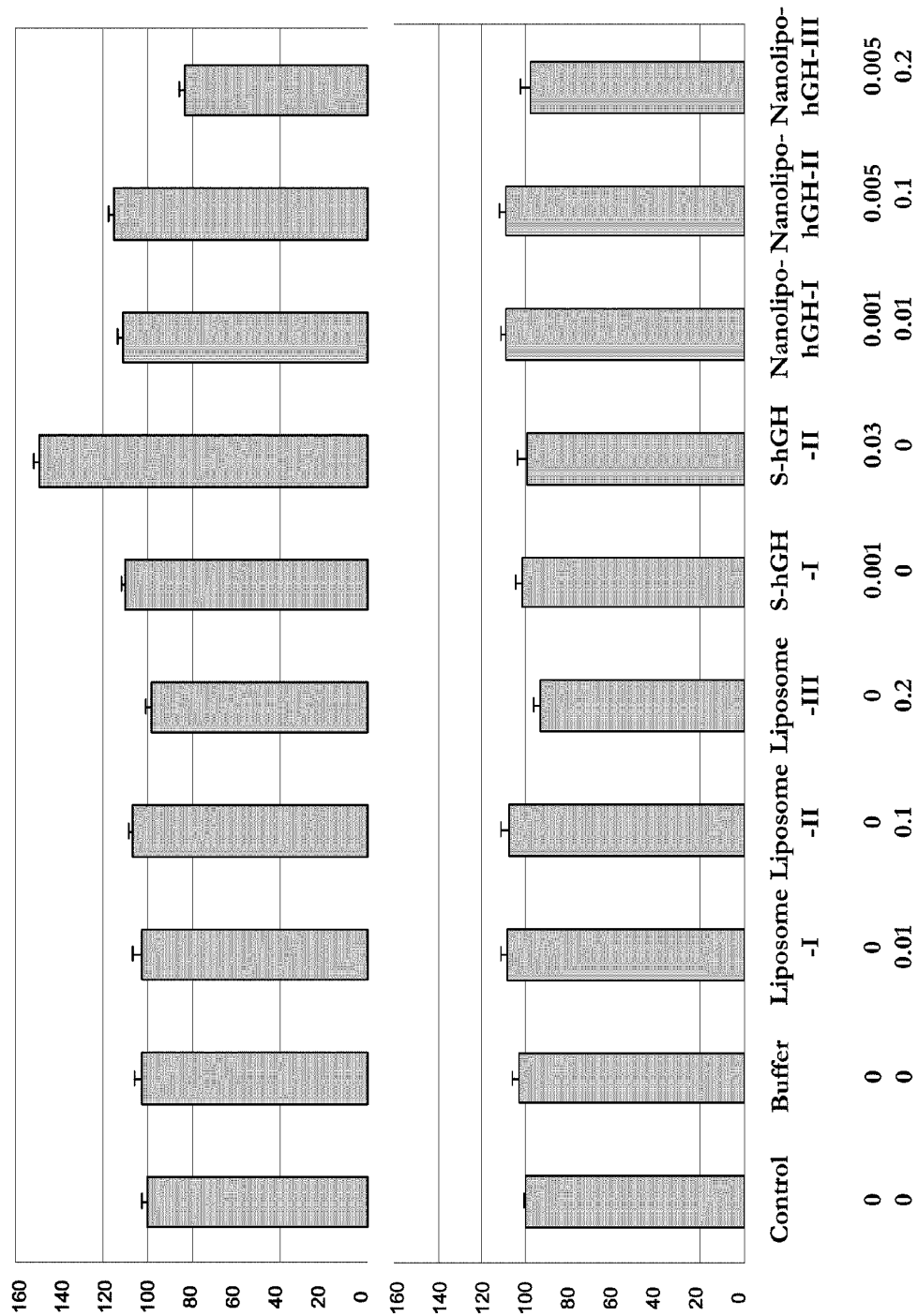
FIG. 7 is a graphic diagram showing the results of the safety test for an hGH-encapsulating liposome of the present invention.

As shown in FIG. 7, the hGH-containing nanoliposome of this invention has no effect on the cell viability of HaCaT and HEF, indicating that it is a significantly safe formulation to organisms.

Example VII

Analysis for $Nb_2$ Cell Proliferation by Nanoliposome Formulation Nanolipo-hGH To the well of a 96-well plate containing 50 µl of the $Nb_2$ noble rat lymphoma cell line (NIBSC ECACC #97041101) at a concentration of $1\times10^5$ cells/ml, S-hGH (standard human growth hormone, NIBSC code 98/574), added a sample containing S-hGH and a 1000-fold dilution of a pretreated solution [obtained by disrupting a liposome without human growth hormone using a sonicator and adding a solution (containing 50 mM Tris-Cl pH 8.0, 1 mM EDTA, 8 M urea, 2% Tween 20) thereto in the same volume as the sample and then pipetting the mixture], or a sample containing a 1000-fold dilution of the Nanolipo-hGH (N-hGH; formulation B prepared in Example I) subjected to a sample pretreatment process [disrupting a liposome solution containing human growth hormone with a sonicator and adding a solution (containing 50 mM Tris-Cl pH 8.0, 1 mM EDTA, 8 M urea, 2% Tween 20) thereto in the same volume as the sample and then pipetting the mixture]. Each of the samples was cultured in a 5% $CO_2$ incubator at 37□ for 5 days, and the amount of the proliferated cells was measured using MTT. The mean absorbance of the group containing hGH was calculated as a value relative to the mean absorbance of the control group containing no hGH, taken as 100%.

Figure 8:
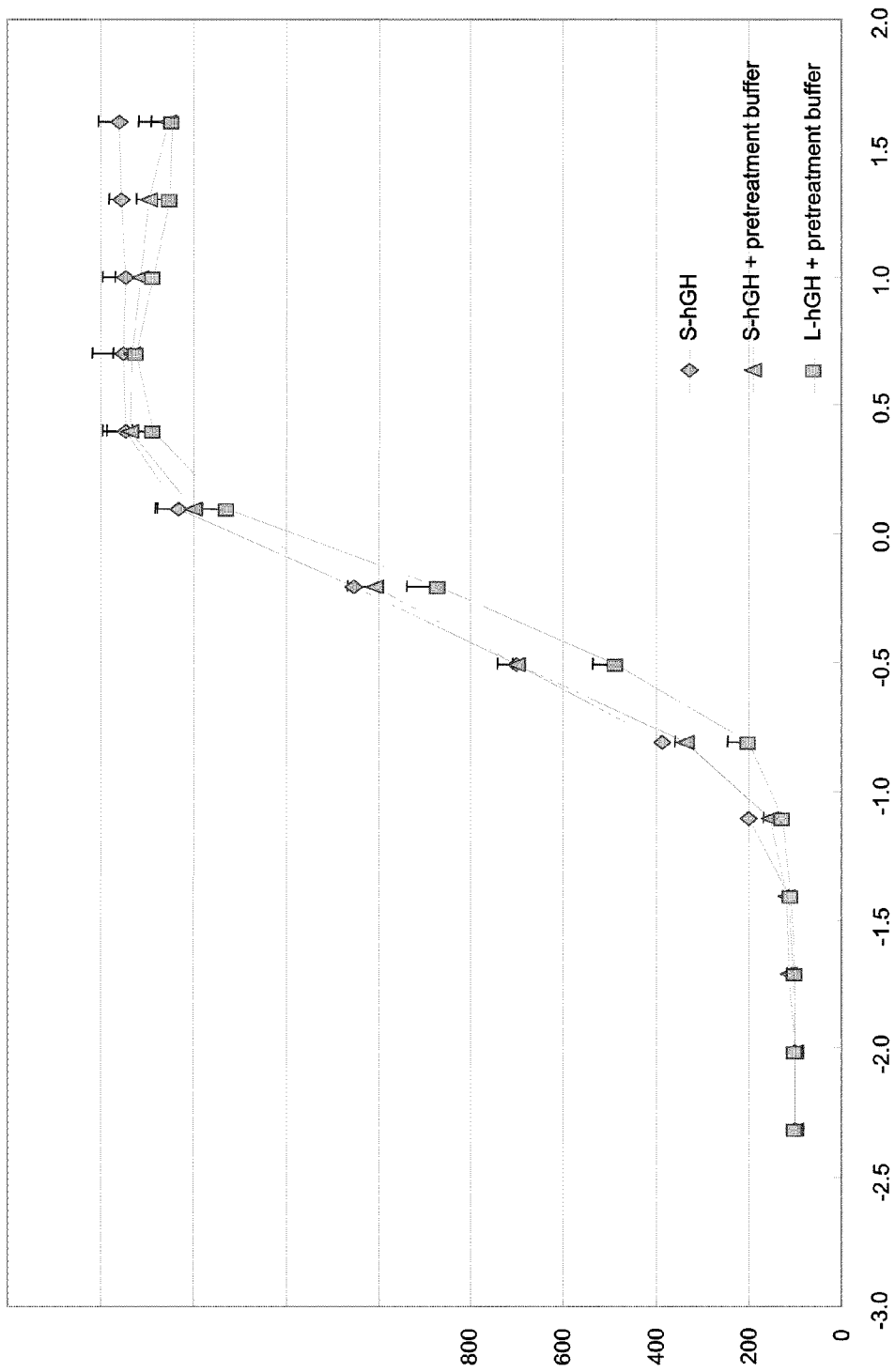
FIG. 8 shows analysis results for the activity of human growth hormone encapsulated in an hGH-encapsulating liposome of this invention.

As shown in FIG. 8, it could be recognized that human growth hormone encapsulated in the Nanolipo-hGH of this invention maintains its original activity.

Example VIII

Analysis of Particle Size Distribution

Figure 9:
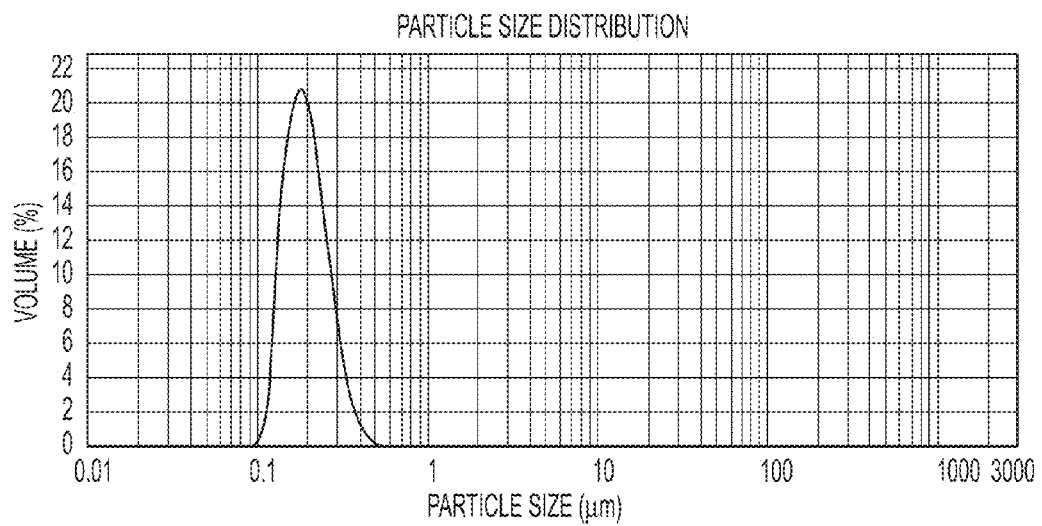
FIG. 9 shows analysis results for the particle size distribution of an hGH-encapsulating nanoliposome of this invention.

The Nanolipo-hGH of formulation B separated by gel permeation chromatography in the above Example was analyzed for particle size distribution at a refractive index of 1.52 using a particle size analyzer (Mastersizer 2000/Malvern Instruments Ltd.) (see FIG. 9). As represented in FIG. 9, the Nanolipo-hGH of this invention shows the largest distribution at a particle size of 0.193 μm, addressing that the Nanolipo-hGH of formulation B is present in the nanometer size.

Example IX

Analysis of Wrinkle-Improving Efficacy 4-week-old nude mice (purchased from Korea Research Institute of Chemical Technology) were tested using the Nanolipo-hGH (N-hGH) of formulation B in Example I. An animal breeding chamber was kept at temperature of 22±2° C. and a humidity of 55-60% in a 12-hr light/12-hr dark cycle, and the animals were permitted free access to solid feed (Central Lab. Animal Inc., Seoul, Korea) and water sterilized by irradiation and were acclimated for about 2 weeks. In order to induce wrinkles on the back of these nude mice, 20 mJ of UVB was irradiated to the mice three times a week for 8 weeks. Then, to the UVB-irradiated back, each of a sample solution and a control solution was applied using a cosmetic brush for 8 weeks. Then, a wrinkle-improving efficacy was evaluated according to the Donald method (Hyun-Seok Kim et. al, Mech. Ageing Dev. (2005. 8.16 In press)).

Figure 10:
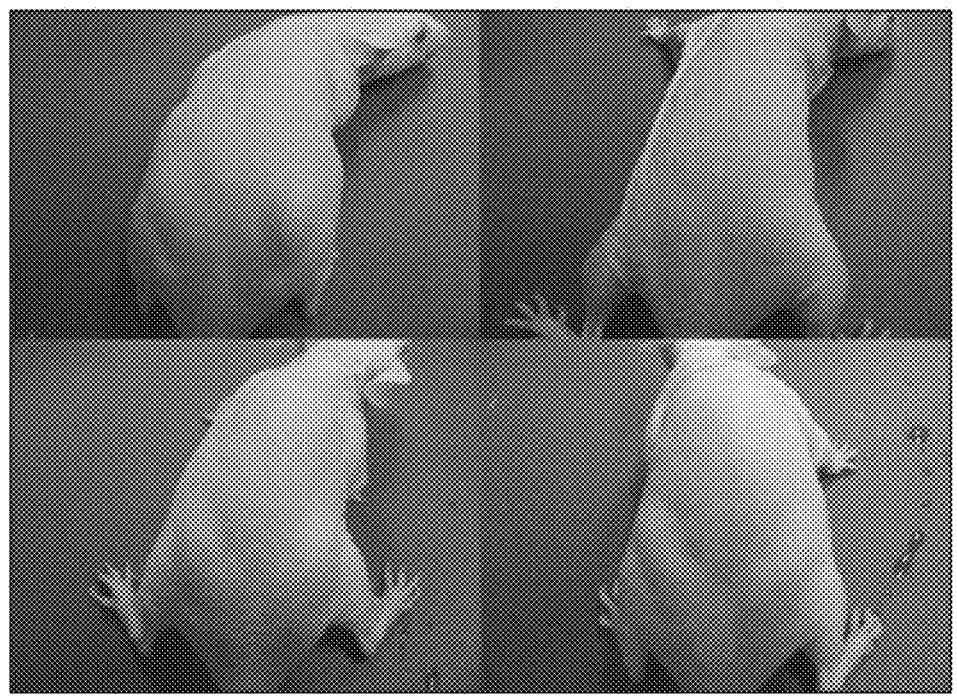
FIG. 10 shows test results for the wrinkle-improving effect of the present hGH-encapsulating liposome on nude mice having UV-induced wrinkles.
Figure 11:
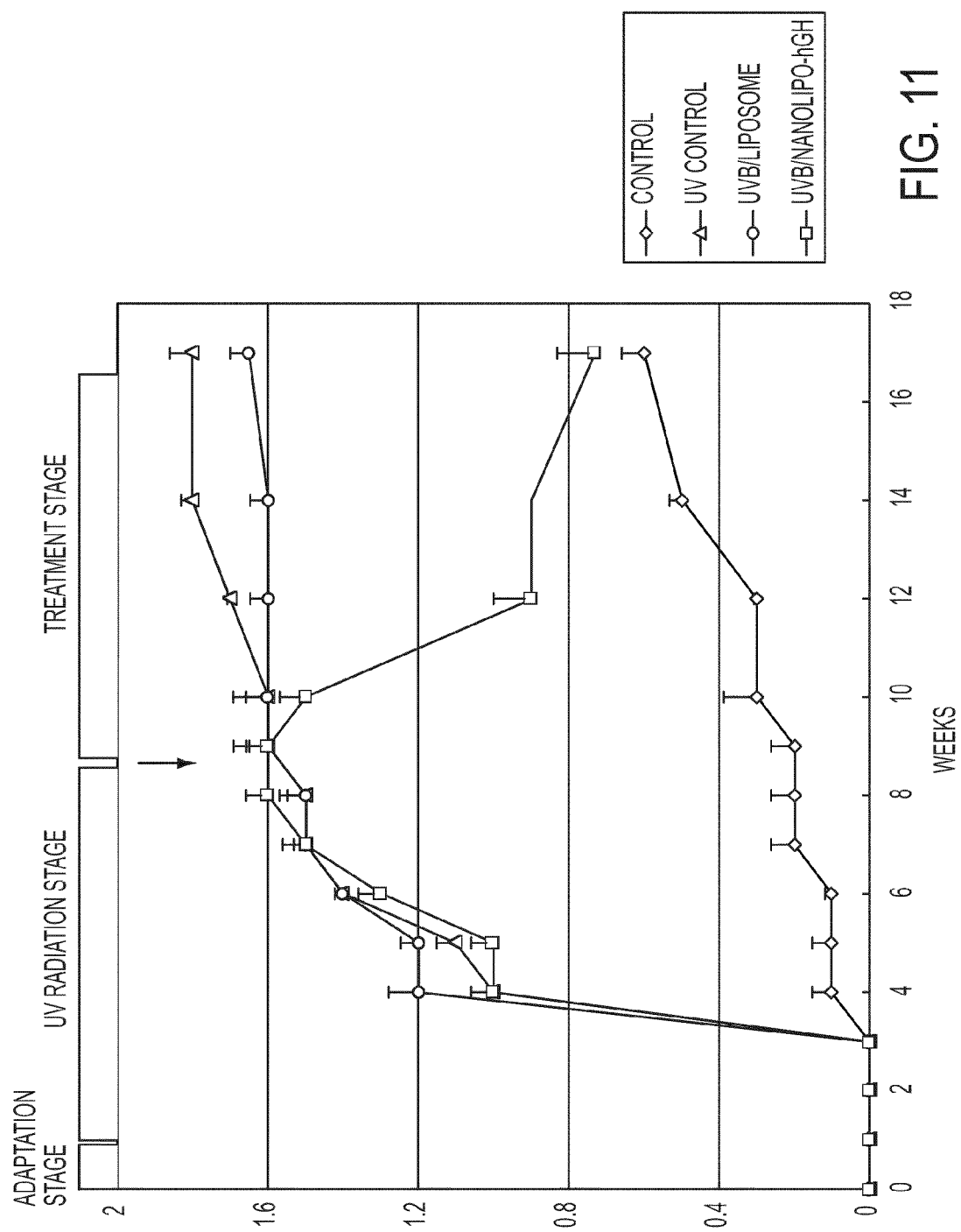
FIG. 11 is a graphic diagram showing the wrinkle-improving effect of the present hGH-encapsulating nanoliposome.

The results are shown in FIGS. 10 and 11. In FIG. 10, the control group (n=3) was not treated, the UVB-control group (n=3) was treated with 20 mJ of UVB to induce only wrinkles, the liposome (n=3) was treated with 20 mJ of UVB to induce wrinkle followed by the treatment with liposome, and the Nanolipo-hGH (n=3) was treated with 20 mJ of UVB to induce wrinkles followed by the treatment with the Nanolipo-hGH of this invention. As shown in FIGS. 10 and 11, the Nanolipo-hGH of this invention exerts effects to effectively eliminate the UV-induced wrinkles, which was clearly observed from about 2 weeks after the topical application of the present Nanolipo-hGH.

Example X

Analysis of Acne Treatment Efficacy

The acne treatment effect of the present human growth hormone-containing liposome was examined in accordance with the following process:

Sixty 15- to 40-year-old women who had acne symptoms on their faces were randomly divided into three groups, and then allowed to use each of the hGH-containing liposome formulation B of Example I (formulation 1), a comparative solution containing only liposome (formulation 2) and a comparative buffer solution (formulation 3) after face washing twice (morning and evening) a day for 3 weeks. There was no particular limitation on usually used cosmetics. Then, the improvement of acne was evaluated based on the user's opinion according to the following criteria. The results are summarized in Table 1. Evaluation criteria: +++ (showing excellent improvement efficacy); ++ (showing significant improvement efficacy); + (showing slight improvement efficacy); ± (not showing improvement efficacy but not showing aggravation efficacy); and − (showing aggravation efficacy).

TABLE 1

| Application Period | Formulation 1 | Formulation 2 | Formulation 3 |
|---|---|---|---|
| 1st week | + | ± | ± |
| 2nd week | ++ | + | ± |
| 3rd week | +++ | + | ± |

As indicated in Table 1, the formulation of this invention has a very good effect on the improvement of acne, which became evident 2 weeks after the application of the formulation. Furthermore, the formulation of this invention does not substantially cause irritation to the skin, for example, erythema or itching.

Example XI

Analysis of Dark Spot Removal Efficacy

The dark spot removal effect of the present human growth hormone-containing liposome was tested in the following manner:

Sixty 40- to 60-year-old women were randomly divided into three groups, and then allowed to use each of the hGH-containing liposome formulation B of Example I (formulation 1), a comparative solution containing only liposome (formulation 2) and a comparative buffer solution (formulation 3) after face washing twice (morning and evening) a day for 8 weeks. There was no particular limitation on usually used cosmetics. The improvement of dark spots was evaluated based on the user's opinion according to the following criteria. The results are summarized in Table 2. Evaluation criteria: +++ (showing a very good improvement efficacy); ++ (showing a significant improvement efficacy); + (showing a slight improvement efficacy); ± (showing no improvement efficacy but not showing aggravation efficacy); and − (showing aggravation efficacy).

TABLE 2

| Application Period | Formulation 1 | Formulation 2 | Formulation 3 |
|---|---|---|---|
| 1st week | ± | ± | ± |
| 2nd week | ± | ± | ± |
| 3rd week | + | ± | ± |
| 4th week | + | ± | ± |
| 5th week | ++ | + | ± |
| 6th week | ++ | + | ± |
| 7th week | ++ | + | ± |
| 8th week | ++ | + | ± |

As indicated in Table 2, the formulation of this invention has a significantly excellent effect on the improvement of dark spots, which started to be clearly shown from about 3-5 weeks after the application of the formulation. Furthermore, the present composition did not substantially cause irritation to the skin, for example, erythema or itching.

Example XII

Analysis of Localization of Nanoliposome Formulation Nanolipo-hGH and Effect Thereof on Skin The abdominal region of a Sprague Dawley rat was divided into six zones (circles each having a radius of 1 cm) and treated with the following samples: 0.1% methyl-paraben buffer solution, 0.1% liposome, 0.001 U hGH, 0.0001 U hGH, 0.001 U Nanolipo-hGH, and 0.0001 U Nanolipo-hGH.

The animal was treated with each of the samples in an amount of 50 µl twice at 24-hour intervals seven times in total. At 24 hours after treatment with the last sample, tissue was dissected from the rat. The dissected tissue was sectioned in a thickness of 40 µm and treated with a polyclonal rabbit anti-human growth hormone primary antibody (DAKO, U.S.A.) and then with a biotin-conjugated anti-rabbit secondary antibody (VECTOR. VECTASTAIN ABC kit (RABBIT IgG), U.S.A.) at room temperature for 30 min. Next, the sectioned tissue was treated with a VECTASTAIN ABC reagent (VECTOR, U.S.A.) at room temperature for 30 min and subjected to a color development reaction with a DAB substrate (Diaminobenzidine, Sigma, USA). The sectioned tissue was dehydrated with 78% ethanol, 85% ethanol and 95% ethanol in order and then treated with xylene for 5 min. The tissue was fixed on a slide glass, and then the location of human growth hormone contained in Lipo-hGH was observed.

Figure 12A:
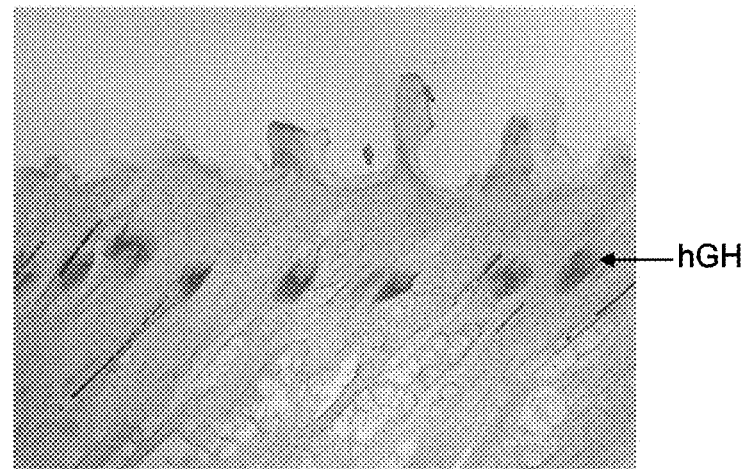
FIG. 12a is a photograph showing the localization of human growth hormone, which occurs when the present hGH-encapsulating nanoliposome is delivered to the skin through hair follicles in Sprague Dawley rats.

As shown in FIG. 12a, the human growth hormone encapsulated in the present Nanolipo-hGH or the rat growth hormone originated from the rat is found at locations considered as bulge stem cells of hair follicles.

Figure 12B:
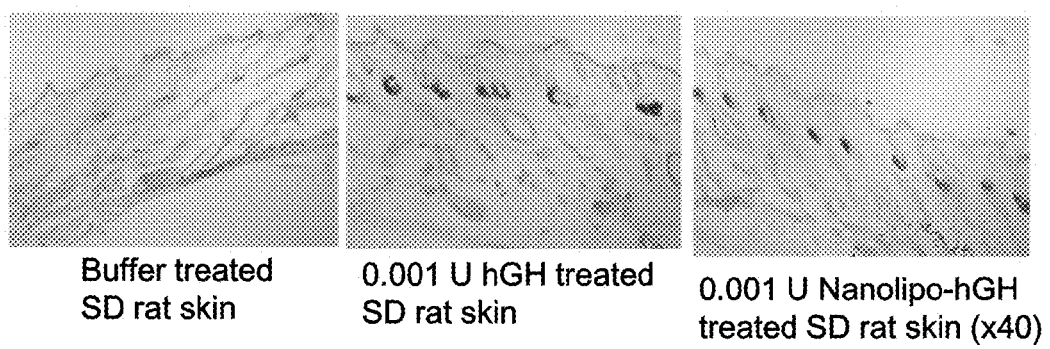
FIG. 12b is a photograph showing the effect of the present hGH-encapsulating nanoliposome on the dermal layer and hair follicles of the skin of Sprague Dawley rats.

In addition, it could be appreciated that the dermal layer of the rat skin applied with the present Nanolipo-hGH (containing 0.0001 U hGH) becomes widened and the number of hair follicles on the dermal layer is increased, as represented in FIG. 12b. Furthermore, it could be found in FIG. 12b that, where only the hGH aqueous solution was applied to the skin, hGH reached the location of bulge stem cells in hair follicles, which is a very surprising finding, considering the state of art and common knowledge in the art. These results suggest a promising improvement in skin conditions by applying to the skin not only hGH encapsulated in liposomes but also an hGH aqueous solution itself.

Example XIII

Analysis of Effects of Nanoliposome Formulation Nanolipo-hGH on Mouse Skin

The effect of the nanoliposome formulation Nanolipo-hGH (prepared in Example I) on the skin of ICR mice was analyzed by H&E (Hematoxylin & Eosin) staining. For this purpose, after removing the hairs of the back of ICR mice, the back regions divided with respect to the vertebra were treated with a control group and the present Nanolipo-hGH at 4-hr intervals for 2 weeks: group 1 (n=3); untreated group 2 (n=3); a group (n=3) treated with liposome/0.1 U of the present Nanolipo-hGH; group 3 (n=3) treated with liposome/0.01 U of the present Nanolipo-hGH; group 4 (n=3) treated with liposome/0.001 U of the present Nanolipo-hGH. After 2 weeks of the treatment, tissues were dissected from the mice. The dissected tissues were paraffinized and sectioned in a thickness of 4 µm, and the sectioned tissues were placed on a slide glass. Then, the sections were deparaffinized and treated with a hematoxylene solution at room temperature for 10 min and then with an eosin solution at room temperature for 1 min. Next, the sections were dehydrated with 78% ethanol, 85% ethanol, 95% ethanol and 100% ethanol in order and then treated with xylene for 5 min. The tissues were immobilized and then the stained tissues were observed under a microscope.

Figure 13A:
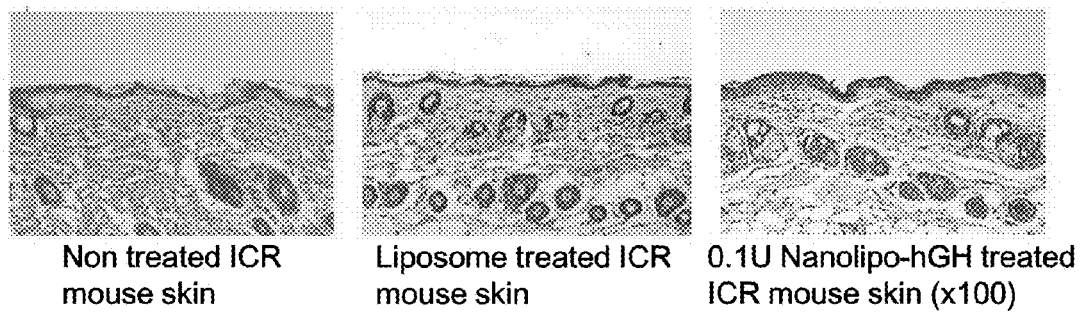
FIG. 13a is a photograph showing the effect of the present hGH-encapsulating nanoliposome on the epidermis and dermis of the skin of ICR mice.
Figure 13B:
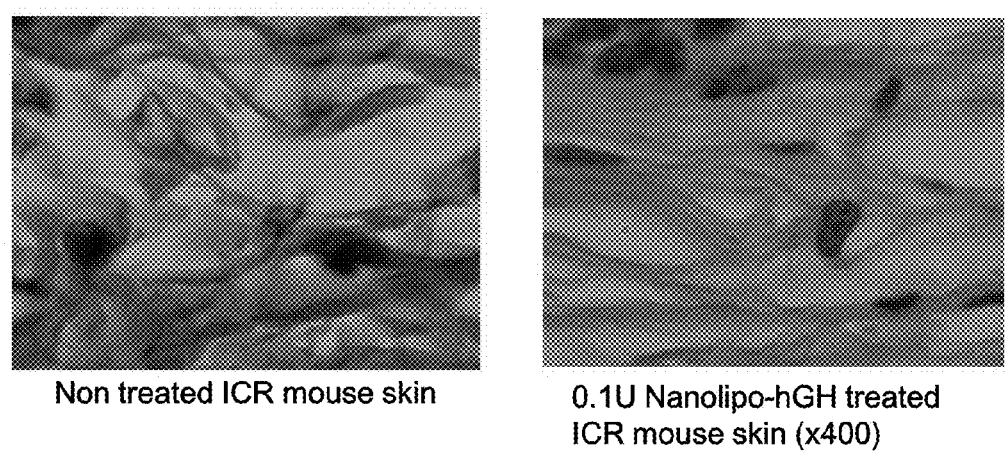
FIG. 13b is a photograph demonstrating that the present hGH-encapsulating nanoliposome induces the remodeling of connective tissue in the dermal layer of ICR mice.

As represented in FIG. 13a, the proliferation of cells in the epidermal layer of the skin treated with the present nanoliposome formulation Nanolipo-hGH is greatly increased, and the remodeling of connective tissues in the dermal layer occurs to form more compact connective tissues. FIG. 13b, a photograph taken under 400× magnification, shows more evidently that the remodeling of connective tissues in the dermal layer occurs.

Example XIV

Analysis of Effect of Nanoliposome Formulation Nanolipo-hGH on Artificial Skin

Neoderm-ED™ (Tego Science, South Korea) was used to analyze the effect of the present nanoliposome formulation Nanolipo-hGH on artificial skin. Neoderm-ED™ is a human skin model for in vitro tests and consists of an epidermal and dermal matrix. Test groups were as follows: group 1 untreated; group 2 treated only with a buffer solution; groups 3 and 4 treated with liposome; and groups 5 and 6 treated with 0.001 unit and 0.01 unit, respectively, of the present Nanolipo-hGH. Paraffin embedding and H&E staining were performed in the same manner as in the above Example. Finally, the stained tissues were observed under a microscope.

As shown in FIG. 14, cells in the keratinocyte layer of Neoderm-ED™ treated with the present nanoliposome formulation Nanolipo-hGH were actively proliferated.

Example XV

Figure 15:
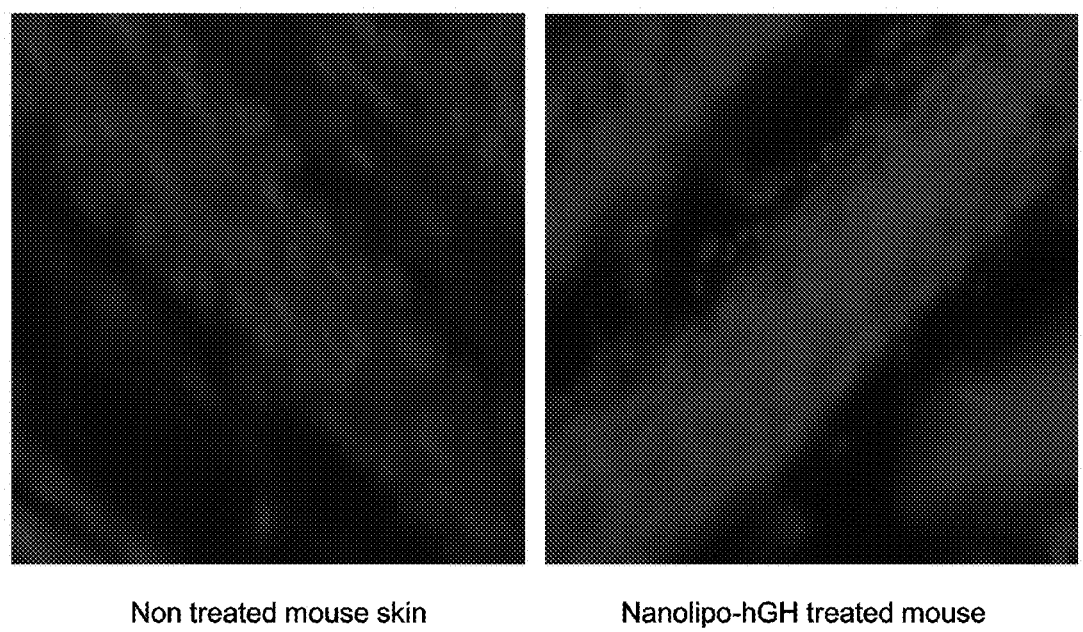
FIG. 15 is a photograph showing the results of immunohistochemical analysis conducted to examine the location of hGH delivered to hair follicles with the aid of the present hGH-encapsulating nanoliposome.

Localization of hGH to Hair Follicle Delivered by Nanoliposome Formulation Nanolipo-hGH 8-week-old C57BL/6 mice (Jung Ang Lab Animal Inc., South Korea) in the telogen stage were anesthetized with ketamine (Yuhan Corp.) and rompun (Bayer Korea Ltd.), and the hairs of their back were removed with a depilatory. The divided portions of the back were treated with 150 µl of each of 0.1 U Nanolipo-hGH and 0.1 U hGH twice a day for 19 days. From 4 hr before collecting tissues, the portions were treated at 30-minute intervals. The collected tissues were fixed in 10% formalin solution, and paraffin blocks were prepared and sectioned to a size of 10 µm. The sections were treated with a polyclonal rabbit anti-human growth hormone primary antibody (DAKO, U.S.A.) for 12 hr and then with a Texas-Red fluorescence-conjugated anti-rabbit secondary antibody (VECTOR) at room temperature for 1 hr and 30 min. Then, a DAPI-containing mounting medium (VECTOR) was dropped, and the sections were covered with a cover glass and observed under a fluorescent microscope. As shown in FIG. 15, hGH spots stained red could be identified along the outer root sheath in the hair follicles of the skin treated with Nano-lipo-hGH.

Having described a preferred embodiment of the present invention, it is to be understood that variants and modifications thereof falling within the spirit of the invention may become apparent to those skilled in the art, and the scope of this invention is to be determined by the appended claims and their equivalents.

What is claimed is:

1. A method for preparing a nanoliposome encapsulating a protein, comprising the steps of:
   (a) preparing a dispersion by dispersing a phospholipid in an aqueous solution containing the protein;
   (b) applying a shearing force to the dispersion;
   (c) adding an additional amount of the phospholipid to the result of step (b) and then applying a shearing force higher than that of step (b); and
   (d) repeating step (c) with an additional amount of the phospholipid and a shearing force higher than a prior step to obtain the nanoliposome having a diameter and an encapsulation efficiency of interest.

2. The method according to claim 1, wherein the protein is one or more selected from the group consisting of a hormone, a hormone analog, an enzyme, an enzyme inhibitor, a signal transduction protein or fragment thereof, an antibody or fragment thereof, a peptide, an antigen, an adhesive protein, a structural protein, a regulatory protein, a toxin protein, a cytokine, a transcription regulatory protein, a blood clotting protein and a plant defense-inducing protein.

3. The method according to claim 2, wherein the protein is human growth hormone.

4. The method according to claim 1, wherein the phospholipid is one or more selected from the group consisting of soybean lecithin, distearoylphosphatidylcholine, hydrogenated soybean lecithin, egg lecithin, dioleoylphosphatidylcholine, hydrogenated egg lecithin, dielaidoylphosphatidylcholine, dipalmitoylphosphatidylcholine and dimyristoylphosphatidylcholine.

5. The method according to claim 1, wherein the phospholipid is hydrogenated soybean lecithin.

6. The method according to claim 1, wherein the application of the shearing force is performed using a high pressure homogenizer, a sonicator, a microfluidizer, an extrusion apparatus or a French press.

7. The method according to claim 6, wherein the application of the shearing force is performed using the high pressure homogenizer.

8. The method according to claim 7, wherein the application of a stepwise increased shearing force executed by steps (b)-(d) is performed using the high pressure homogenizer with increasing a pressure up to 1200 bar.

9. The method according to claim 8, wherein the pressure of the high pressure homogenizer is increased stepwise by 50-200 bar per each application of the shearing force in steps (b)-(d).

10. The method according to claim 1, wherein the final amount of the phospholipid present in the dispersion is 30 w/v (%).

11. The method according to claim 10, wherein the amount of the phospholipid is increased stepwise by 1-5 w/v (%) per each addition of the phospholipid in steps (b)-(d).

12. The method according to claim 1, wherein the finally formed nanoliposome has the diameter of 50-350 nm.

13. The method according to claim 1, wherein the finally formed nanoliposome has the structure of a small unilamellar vesicle.

14. The method according to claim 1, wherein the finally formed nanoliposome is in the form of liquid.

15. The method according to claim 1, wherein the protein encapsulated in the finally formed nanoliposome has an activity corresponding to 90-100% of the activity of the protein prior to encapsulation.

* * * * *